United States Patent [19]
Ayers

[11] Patent Number: 6,004,436
[45] Date of Patent: *Dec. 21, 1999

[54] PROCESSES FOR THE CHEMICAL MODIFICATION OF INORGANIC AEROGELS

[75] Inventor: Michael Ayers, El Cerrito, Calif.

[73] Assignee: The Regents of the University of California, Oakland, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/698,980

[22] Filed: Aug. 16, 1996

[51] Int. Cl.[6] .............................. C07C 1/00; C01B 53/00; C01B 25/00; B05D 3/04

[52] U.S. Cl. ............................... 204/157.15; 204/157.43; 204/157.45; 204/157.47; 204/157.48; 204/157.51; 204/157.74; 204/157.81; 423/338

[58] Field of Search ............................ 204/155, 157.43, 204/157.44, 157.45, 157.47, 157.48, 157.5, 157.51, 157.63, 157.64, 157.74, 157.81, 157.15; 423/338

[56] References Cited

U.S. PATENT DOCUMENTS

| | | | |
|---|---|---|---|
| 4,610,863 | 9/1986 | Tewari et al. | 423/338 |
| 4,629,652 | 12/1986 | Carlson et al. | 428/304.4 |
| 5,306,445 | 4/1994 | Reed et al. | 252/646 |
| 5,313,485 | 5/1994 | Hamil et al. | 372/69 |
| 5,314,857 | 5/1994 | Koontz | 502/258 |
| 5,358,776 | 10/1994 | Hotaling | 428/304.4 |

FOREIGN PATENT DOCUMENTS 2141418  12/1984  United Kingdom.

*Primary Examiner*—Kathryn L. Gorgos
*Assistant Examiner*—Edna Wong
*Attorney, Agent, or Firm*—Paul R. Martin; Henry Sartorio; David J. Aston

[57] ABSTRACT

A process is described to modify the chemical structure of an aerogel under conditions which inhibit plasma formation within the aerogel pores, which process includes; (a) providing an aerogel with a pore size of less than $0.1\mu$; (b) exposing the initial aerogel to at least one gas selected from the group consisting of reducing gas, oxidizing gas, noble gas and combinations thereof, with the proviso that at least one reducing gas or one oxidizing gas is present; and (c) irradiating the combination of step (b) while maintaining the temperature to preserve the structural composition of the aerogel at a pressure of between about 0.1 and 54 Torr for between and about 5 and 960 minutes. This process produces a modified aerogel wherein the pore size does not allow for plasma formation within the pore. Chemical reactions occur within the pores of the aerogel of a nonplasma nature. These modified aerogels have a number of uses, including catalysts, ceramics, composites, chemical sensors, LED's and the like.

17 Claims, 3 Drawing Sheets

PROCESSES FOR THE CHEMICAL MODIFICATION OF INORGANIC AEROGELS

BACKGROUND OF THE INVENTION

Origin of the Invention

This invention was made in the course of or under contract no. DE-AC03765F00098 between the U.S. Department of Energy and the University of California. The government has certain rights in this invention.

Field of the Invention:

The present invention concerns a process for altering the chemical composition of aerogels without affecting their morphological properties and under conditions which inhibit formation of a plasma within the aerogels' pores. Specifically, the aerogels are exposed to gas and irradiated at optimal temperatures and pressures.

Description of Related Art:

Present processes to produce inorganic aerogels are limited to the synthesis of oxides of metals and metalloids or pure carbon aerogels. Currently, there are no synthetic routes to non-oxide inorganic aerogels, such as metal carbides, nitrides, silicides, and halides.

General methods of preparing aerogels have been known as early as the 1930's. See, for example S. S. Kistler, in *Nature* 127:741 (1931) and S.S. Kistler in U.S. Pat. No. 2,249,767 both of which describe the preparation of silicon dioxide aerogels. The methods in Kistler involve techniques which were considered laborious and dangerous at that time, including drying gels formed from sodium silicate and removing solvents by supercritical extraction. Because of the hazards involved with Kistler's process, there was very little progress in aerogel research for several decades thereafter.

In the early 1980's there was a resurgence of aerogel research. Present developments in aerogels have lead to a variety of compositions. However, despite significant advances in aerogel technology, most of the aerogels produced are limited to the oxides of metal or metalloids. See, for example T. M. Tillotson, et al. U.S. Pat. No. 5,409,683. Organic aerogels are also known. See, for example, R. W. Pekala, et al. *J.Non-Cryst. Solids* 145:90 (1922). Methods exist to convert some of these organic aerogels into pure carbon aerogels by pyrolysis in an inert atmosphere. Other processes to prepare aerogels include R. S. Upadhye, et al., U.S. Pat. No. 5,227,239; T. M. Tillotson, et al., U.S. Pat. No. 5,275,796; and C. Colmenares, U.S. Pat. No. 5,030,607. Yet, there is still a need for procedures to produce non-oxide inorganic aerogels and in particular, procedures for making non-oxide aerogel from other types of aerogels.

General procedures for the transformation of metals or metalloid oxides into non-oxide materials have not been successful with aerogels. Such techniques require treatment with a reducing agent at temperatures which are too high to preserve an aerogel's structure. For example, the conversion of $SiO_2$ to $Si_3N_4$ using ammonia occurs at 1450° C. See, T. Ishii, et al. Jap. Pat. #63,162,514 (Jul. 6, 1988). However, silica aerogels will shrink and densify at above 450° C. Therefore, typical procedures to convert metal or metalloid oxides into non-oxide organic aerogels are not useful.

Prior attempts at modifying aerogels are also not applicable to making non-oxide inorganic aerogels. These modification techniques have been restricted to the addition of a single layer or deposits of new material within the aerogel. Such procedures do not significantly change the chemical formula of the aerogels.

Some art of general interest is as follows:

A. J. Hunt, et al. *J Non-Cryst. Solids* Vol. 185, p.227 (1995) disclose chemical vapor infiltration to deposit new material within the aerogel matrix.

H. Yokogawa, et al.*J. Non-Cryst. Solids* Vol. 186, p.23 (1995) disclose a method of affecting one molecular layer of an aerogel, leaving the bulk of the material unchanged.

P. H. Tewari, et al. in U.S. Pat. No. 4,610,863 disclose a process for forming a transparent aerogel as an insulating array.

J. Carlson, et al. in U.S. Pat. No. 4,629,652 disclose a method of production of an aerogel on a support.

S. Reed, et al. in U.S. Pat. No. 5,306,445 (1994) disclose chemical treatment to change one molecular layer of the interior surface of the aerogel.

S. L. Koontz in U.S. Pat. No. 5,314,857 disclose the use of oxygen plasma to remove adsorbed organic material from the interior surface of aerogel powders resulting in the formation of aerogel granules yet not changing the chemical structure of the aerogel.

S. P. Hotaling in U.S. Pat. No. 5,358,776 disclose a plasma processing technique to deposit plasma on a substrate, adding a new material to the substrate but not altering its chemical structure.

W. Cao, et al. in U.S. patent application, Ser. No. 08/221, 643 disclose thermally assisted chemical vapor infiltration to deposit a material on the pores of the aerogel.

J. Maire in GB Patent 2 141 418 A disclose chemical deposition in the vapor phase of carbon in silica aerogels.

None of these references individually or collectively teach or suggest the present invention.

All patents, patent applications, articles, references, publications, standards and the like cited in this application are incorporated herein by reference in their entirety.

There is, therefore, a strong need for alternative methods of modifying aerogels to the presently used chemical treatments in order to change the chemical formula of aerogels and produce non-oxide inorganic aerogels. What is needed is a process which alters the functional properties of aerogels and preserves the original aerogel's morphological properties. Further, the improved methods should circumvent the need for excessively high temperatures during the transformation process.

The present invention has operational and commercial value in that it provides efficient processes for modifying the chemical structure of aerogels thereby changing the aerogel's physical properties yet maintaining the original structural properties. Of special interest is the use of the present process in producing non-oxide inorganic aerogels. Non-oxide inorganic aerogels find application in many fields including catalysts, ceramics, composite materials, chemical sensors (e.g. oxygen, etc.), optical devices, light-emitting devices, microelectronics, energy storage devices, etc.

SUMMARY OF THE INVENTION

The present invention provides a process for modifying the chemical structure of an aerogel under conditions which maintain the integrity of the aerogel's structural properties. Specifically, energized gasses are used to chemically alter the aerogel's backbone.

More specifically, the present invention relates to a process for the modification of the chemical structure of an aerogel under conditions which inhibit the formation of plasma within the aerogel's pores. The modification process comprises:

(a) providing an aerogel with a pore size of less than 0.1 micron;
(b) exposing the aerogel to at least one gas selected from the group consisting of reducing gas, oxidizing gas, noble gas and combinations thereof, with the proviso that at least one of the reducing gas or oxidizing gas is present; and
(c) irradiating the combination of step (b) with electromagnetic radiation for between about 5 and 960 minutes, at a pressure of between about 0.1 and 54 Torr and while maintaining the temperature to preserve the structural composition of said aerogel. Preferably, the temperature is about 200° C. or below.

In one preferred embodiment steps (b) and (c) are optionally repeated one or more times, wherein in step (b) the same or a different gas composition is present.

In another preferred embodiment the irradiation is with microwave or radio frequency radiation. The irradiation optionally includes the addition of a magnetic field.

In still another preferred embodiment, the aerogel is selected from a group consisting of inorganic aerogels including $SiO_2$, $GeO_2$, $SnO_2$, $B_2O_3$, $Al_2O_3$, $TiO_2$, $ZrO_2$, $HfO_2$, $V_2O_5$, $Nb_2O_5$, $Ta_2O_5$, $CrO_3$, $MoO_3$, $WO_3$, $Fe_2O_3$, and lanthanide oxides; carbon; mixed-metal aerogels, including $SiO_2$—$Al_2O_3$, $SiO_2$-$TiO_2$, $BaTiO_3$, $PbTiO_3$, and $NiOAl_2O_3$; and inorganic and mixed-metal aerogel further comprising additional phases. Preferably, the starting inorganic aerogel is selected from $SiO_2$, $Al_2O_3$, $TiO_2$ or $ZrO_2$.

In another preferred embodiment the type of reducing gas which is introduced to the aerogel is selected from a group consisting of $H_2$, $D_2$, $NH_3$, $ND_3$, $N_2$, $NO$, $CO$, $CH_4$, $C_2H_6$, $C_2H_2$, $C_3H_8$ (and other hydrocarbons), $CH_3F$, $B_2H_6$, $B_4H_{10}$, $H_2S$, $H_2Se$, $H_2Te$, $PH_3$, $AsH_3$, $SbH_3$, $SiH_4$, $Si_2H_6$, $SiH_3Cl$, $GeH_4$, $Ge_{26}$, and $SnH_4$. Preferably, the reducing gas is selected from $CH_4$, $H_2$, $NH_3$ or $CO$.

Another preferred embodiment includes oxidizing gas which is selected from a group consisting of $F_2$, $Cl_2$, $Br_2$, $SF_6$, $NCl_3$, $N_2O$, $PF_3$, $SiHCl_3$, $SiF_4$, $OF_2$, and $AsF_5$. Preferably, the oxidizing gas is selected from $N_2O$, $SF_6$ or $Cl_2$.

The aerogel in still another preferred embodiment comprises reducing and/or oxidizing gas which is diluted with noble gas. The noble gas is selected from the group consisting of He, Ne, Ar, Kr, and Xe. Preferably, the noble gas is selected from He, Ne, or Ar.

BRIEF DESCRIPTION OF THE FIGURES

FIG. 1A is a graphic representation of an nuclear magnetic resonance (NMR) spectrum for a untreated silica aerogel. The horizontal is in parts per million (ppm) from tetramethylsilane. The vertical scale is a measure of general intensity. $Q^2$ designates a Si atom having a

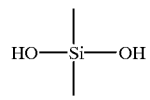

bond. $Q^3$ designates a Si atom having a

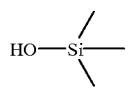

bond. $Q^4$ designates a Si atom having a $(\equiv SiO)_2$—Si—$(OSi\equiv)_2$.

Figure 1A:
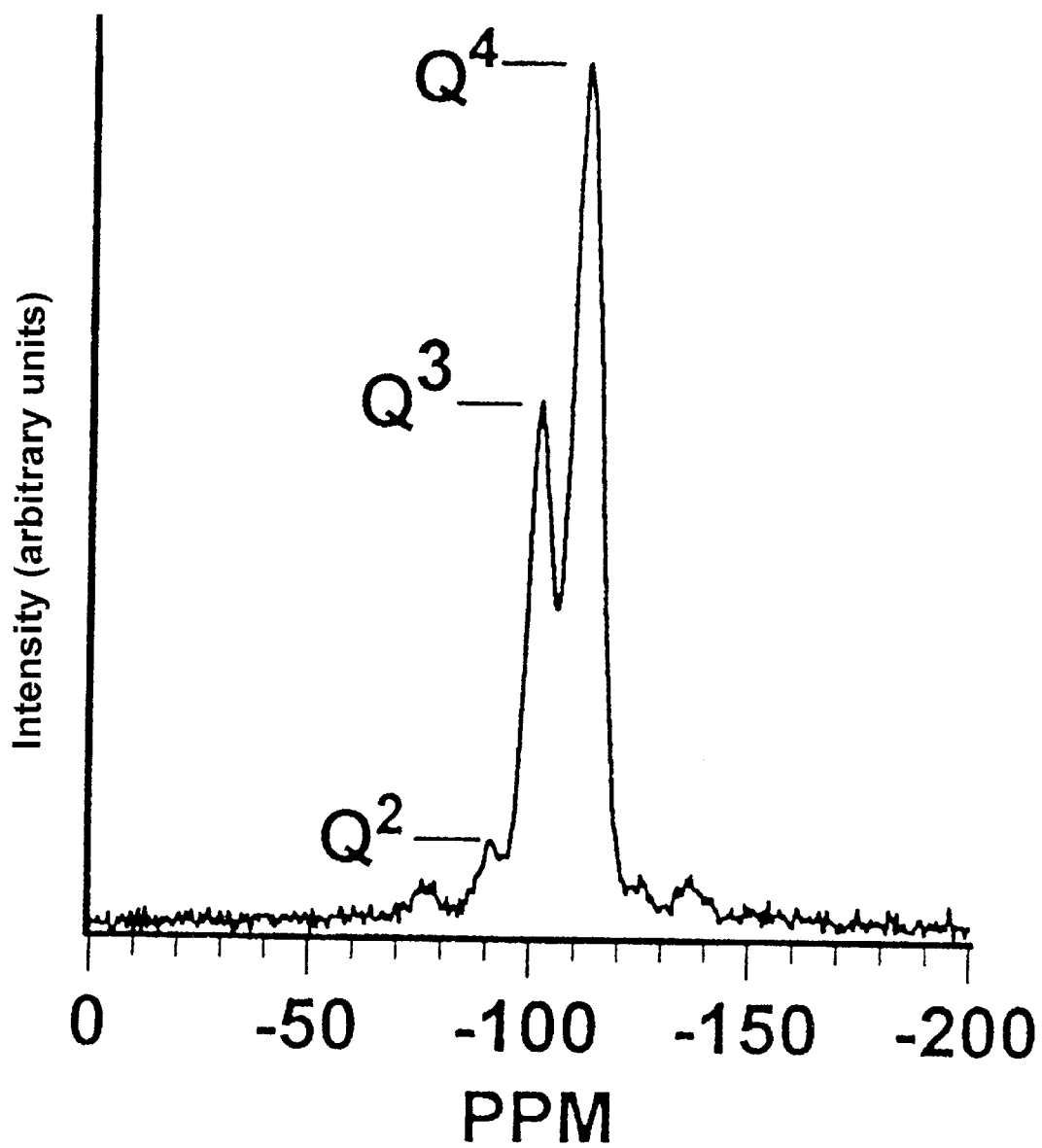
Figure 1B:
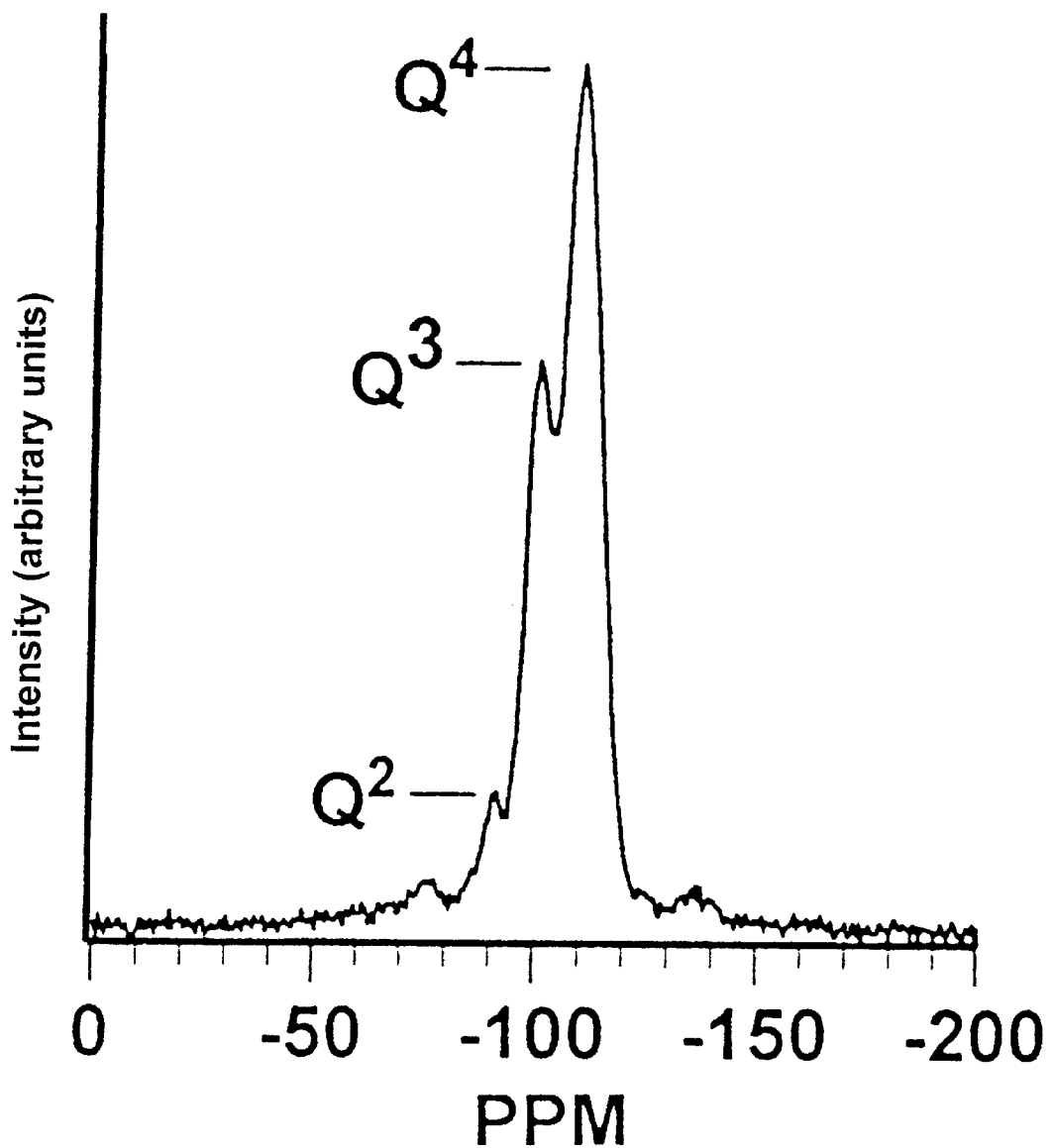

FIG. 1B is a graphic representation of an NMR spectrum for a treated silica aerogel under the same conditions and the ratios are different in intensity.

Figure 2:
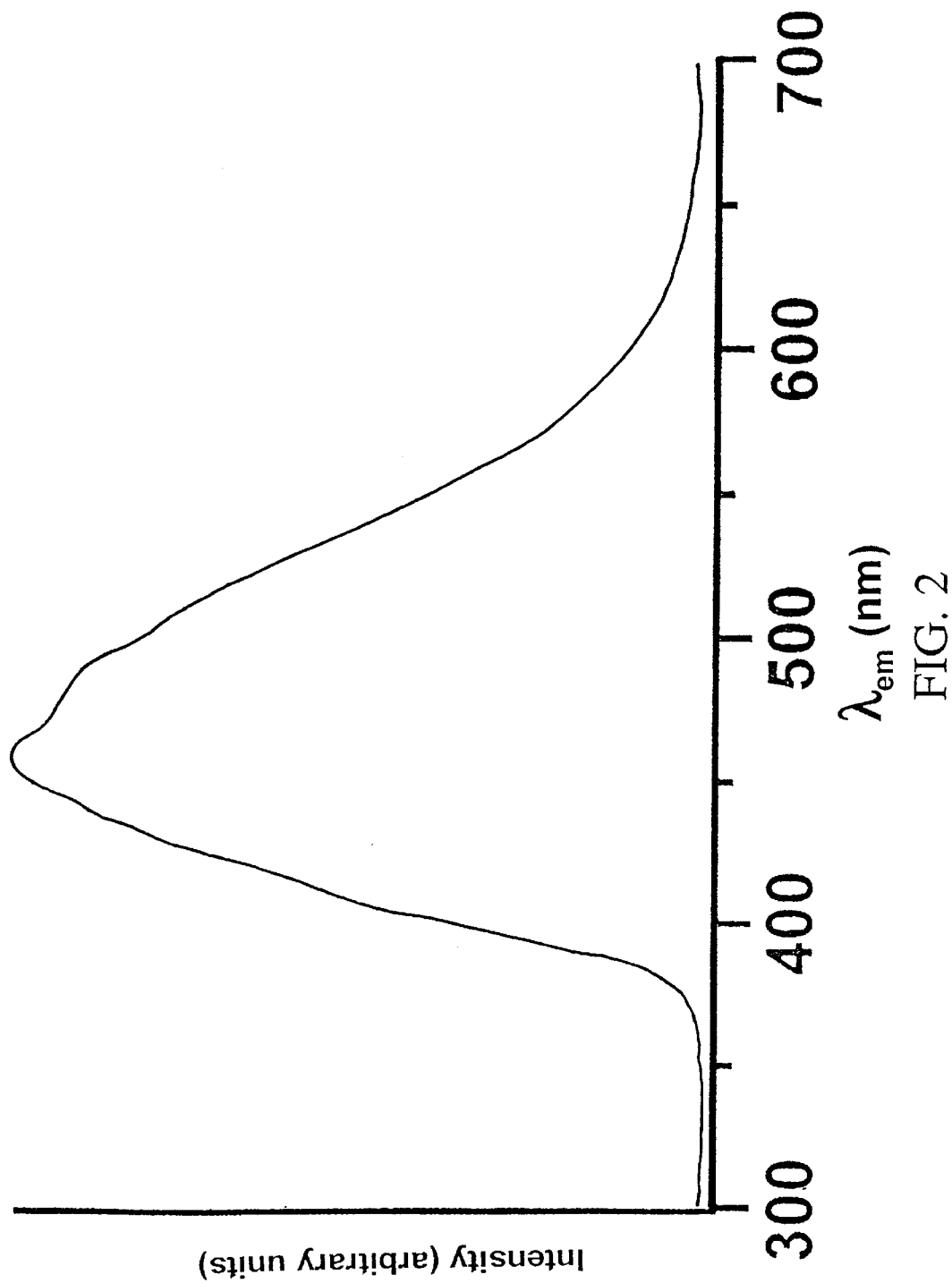

FIG. 2 is a graphic representation of a spectrum of emitted light for a modified silica aerogel which was excited with 330 nm UV light. The UV horizontal scale is the wavelength in nanometers (nm). The vertical scale is a measure of intensity of the light at a particular wavelength.

DETAILED DESCRIPTION OF THE INVENTION AND PREFERRED EMBODIMENTS

Definitions

As used herein:

"Aerogel" refers to the resulting material formed when the liquid part of a gel is removed without damage to the solid part of the gel. Aerogels are most often prepared by supercritical extraction, controlled evaporation, or freeze drying. The aerogel will retain the original shape of the gel, be free of cracks, and occupy at least 50% of the original gel's volume.

"Aerogel composite" refers to an aerogel containing a second solid phase uniformly dispersed throughout the material. The second phase may be microscopic, i.e. nanocrystals and films, or macroscopic, i.e. fibers and powders. It can be added directly to the sol, or after the aerogel has been dried through the vapor phase. "Aerogel microsphere" refers to spherical gels of uniform size. The gels can be dried by the usual methods which are used to form the corresponding aerogels.

"Aerogel powder" refers to aerogel monoliths which are pulverized into powders. On a macroscopic scale, the resulting material consists of small free-flowing granules surrounded by free space. On a microscopic scale, the granules themselves retain the original pore structure of the aerogel. Therefore, aerogel powders possess a bimodal pore structure of large pores between the granules and small pores within the granules.

"Exterior surface" refers to the surface that defines the apparent shape of an aerogel.

"Gel" refers to a material consisting of two parts, solid and liquid generally consisting of a three-dimensional network of solid material and corresponding areas of free space. The solid part results form the agglomeration of sol particles. The liquid part of the gel fills the free space within the solid part. The liquid and solid parts of a gel occupy the same volume of space.

"Hydrocarbon" refers to alkanes, alkenes or alkynes having 1–20 carbon atoms. Preferably, the hydrocarbon has 1 to 10 carbon atoms and is an alkane.

"Interior surface" refers to the surface of the solid particles that make up the microscopic three-dimensional network of the aerogel.

"Microwave (MW)" refers to the region of the electromagnetic spectrum having wavelengths ranging from 0.3 to 30 cm.

"Monolith" refers to a single piece of crack-free aerogel with a definite shape. Aerogel monoliths are made into virtually any shape. Since the solid structure of aerogels consists of a thee-dimensional polymeric network, aerogel monoliths can be thought of as single, extremely large, molecules (e.g. of $SiO_2$).

"Plasma" refers to an ionized, electrically neutral gas formed by the interaction of a typical gas with a strong electric field.

"Pore" refers to a complex porous structure of most aerogels. The pore diameters of silica aerogels range from 2 to 100 nm. However, the pores are open and connected to one another allowing for volatile material to pass from one pore to the next, and eventually through the entire aerogel. As a result, at equilibrium, any atmosphere surrounding an aerogel is identical to that within the aerogel. For example, if an aerogel is placed in a container filled with nitrogen, the aerogel itself will be filled with nitrogen or if an aerogel is placed under vacuum, the pores of the aerogel would be under the same or similar pressure.

"Radio frequency (RF)" refers to the region of the electromagnetic spectrum having wavelengths ranging from 0.3 to 30,000 m.

"Sol" refers to a solution of polymeric or colloidal materials. A sol has many physical properties in common with normal solutions. However, the suspended material can be continuously agglomerating, leading to the formation of a gel.

"Xerogel" refers to a gel that has been dried without using methods that form aerogels. They are often cracked, have much higher densities than aerogels, and are less gas permeable.

As is described above, the available methods of modifying aerogels have significant problems because, for one, they fail to alter the aerogel's chemical formula. The improved process of the present invention encompasses altering the chemical composition of an aerogel using conditions that do not damage the structural properties of the material. The present process is especially useful for synthesizing non-oxide inorganic aerogels, such as metal carbides, nitrides, silicides or halides.

The present invention uses an inorganic aerogel as the initial starting material. The initial aerogel is produced by any conventional procedure. Typically, aerogels are made by sol-gel processing followed by supercritical extraction of entrapped solvents. A combination of reacting fluids and solvents are mixed together to form a gel. To remove the solvent without destroying or altering the solid network, the gel is placed in a vessel and the temperature and pressure are raised above the critical point of the contained solvent. Thereafter, the pressure is released. The resulting material is an aerogel. The preparation methods found in the U.S. patents or articles cited in this application can be used to prepare the initial aerogel structure. For additional information on the preparation of aerogels, See J. Fricke, *J. Porous Materials*, Vol.1, pg. 1 ff, 1995.

The initial aerogel is made of any convenient composition. Aerogels which are composed of oxides of metals and metalloids are of special interest. Some examples of these oxide inorganic aerogels include $SiO_2$, $GeO_2$, $SnO_2$, $B_2O_3$, $Al_2O_3$, $TiO_2$, $ZrO_2$, $HfO_2$, $V_2O_5$, $Nb_2O_5$, $Ta_2O_5$, $CrO_3$, $MoO_3$, $WO_3$, $Fe_2O_3$, lanthanide oxides, carbon, and any combinations thereof. Mixed-metal aerogels may also be used, including $SiO_2$—$Al_2O_3$, $SiO_2$—$TiO_2$, $BaTiO_3$, $PbTiO_3$, and $NiOAl_2O_3$, and any combinations thereof. The aerogel composites may further contain additional phases, e.g. carbon fibers, mineral powders ($TiO_2$, $B_4C$, etc.), metal particles (Ni, Fe, Co, etc.). Where phases are included, the phases may be introduced during the production of the initial aerogel, either prior to or after the supercritical drying step as is described above.

The initial aerogel will have specific morphological properties. The aerogel will be of any convenient size, e.g. thickness, area, etc. and any convenient shape, e.g. cube, spherical, etc. The aerogel will also exhibit any amount of visible transparency.

The aerogel contains a particular network of open and interconnected pores. Prior to its modification, the aerogel's pore structure includes pores of specific diameters. The size of the pores is usually less than about 100 nm and preferably from between about 2 to 100 nm.

The pore is sufficiently small to inhibit the formation of plasma within the internal surfaces of the aerogel. In general, if the pore size is large, a plasma may be produced by the interactions between gas molecules presented during the modification process in the space surrounding the aerogel and exposure to irradiation energy. The pores of the initial aerogel, however, may be up to 10,000 times too small to allow for plasma production. Plasma formation in the present invention, is thereby restricted to the space surrounding the exterior surface of the aerogel. Energetic chemical reactions do occur in the pores, but they are not plasma in origin.

The specific pore structure within the aerogel considerably increases the internal surface of the aerogel relative to its external surface. For example, a piece of silica aerogel in the shape of a cube 1 cm on edge generally has an external to internal surface ratio of $6:800,000$ $cm^2$.

In addition to morphological properties, the initial aerogel has specific functional properties. These properties include distinctive chemical reactivity characteristics, mechanical properties, abilities to form composite materials, electrical properties, magnetic properties, optical properties, and varying resistance to thermal, chemical and radiation damage.

The initial aerogel is modified by first placing the aerogel within a reaction vessel. The volume surrounding and within the aerogel is exposed to a specific gas or gas mixture. One method of exposure is to fill the reaction vessel with the gas. Exposure times will depend on the type of aerogel and gases used.

The type of gas will comprise at least one of reducing or oxidizing gas. Examples of reducing gas include $H_2$, $D_2$, $NH_3$, $ND_3$, $N_2$, NO, CO, $CH_4$, $C_2H_6$, $C_2H_2$, $C_3H_8$ (and other hydrocarbons), $CH_3F$, $B_2H_6$, $B_4H_{10}$, $H_2S$, $H_2Se$, $H_2Te$, $PH_3$, $AsH_3$, $SbH_3$, $SiH_4$, $Si_2H_6$, $SiH_3Cl$, $GeH_4$, $Ge_2H_6$, and $SnH_4$. Preferably, the reducing gas is selected from $CH_4$, $H_2$, $NH_3$ or CO.

Examples of oxidizing gas include $F_2$, $Cl_2$, $Br_2$, $SF_6$, $NCl_3$, $N_2O$, $PF_3$, $SiHCl_3$, $SiF_4$, $OF_2$, and $AsF_5$. Preferably the oxidizing gas is selcted from $N_2O$, $SF_6$ or $Cl_2$.

At least one of reducing or oxidizing gas must be present. The gas may further be diluted with noble (inert) gas, such as He, Ne, Ar, Kr, and Xe. Preferably the noble gas is selected from He, Ne or Ar.

The gas mixture may also include any convenient combination of reducing, oxidizing and noble gases.

The aerogel is next exposed to irradiation from any conventional electromagnetic radiation transmitter source. The type of radiation used preferably has a wavelength in the microwave or radio frequency energy range and has the corresponding frequency. The frequency of the radiation is preferably a frequency that is not absorbed by the aerogel sample.

The length of time which the aerogel is irradiated is between about 5 and 960 minutes, preferably between about 5 and 450 minutes and more preferably for between about 5 to 60 minutes. During exposure to the strong electric field, the temperature of aerogel speed is maintained to preserve the structural composition of the aerogel. If the aerogel is subjected to high temperatures (e.g. above 200° C.), the aerogel may shrink, crack or melt. The optimal temperature depends on the type of aerogel but usually the temperature remains low relative to the conditions needed to allow solid-gas reactions with aerogels. Typically the aerogel temperature is maintained at between about 50 to 200° C., preferably between about 75 to 175° C., and more preferably between about 100 to 150° C.

The pressure of the aerogel is maintained at an optimal value by employing standard vacuum-gas handling equipment. Usually the pressure is at between about 0.1 and 54 Torr, preferably between about 0.5 and 30 Torr and more preferably between about 1.0 to 10 Torr.

In addition, a magnetic field is optionally provided with the microwave or radio frequency. The magnetic field may be produced by an external magnet such as a permanent magnet or electromagnet (e.g. between about 0.5 and 1.0 tesla).

While applicants do not want to be bound by theory, the radiation apparently interacts with the gas, thus moving the atoms and molecules of the gas into excited states, and causing bond dissociation and ionization. The extent of these effects depends on the power of the system and the nature of the gas being used. It appears that these excited species collide and chemically react with the solid material of the aerogel to alter the chemical composition of the aerogel.

The above described procedure may be performed as a batch or sequential process. Thus, where desired, the aerogel sample may be simultaneously exposed to gas and radiation. Stepwise treatment with gas and radiation may also employed. The steps of exposing the aerogel with gas and irradiating is optionally repeated one or more times, as desired. During repeated exposures to gas, the type of gas may be varied or remain the same. For example, the same gas may be introduced to the aerogel several times, followed by a single irradiation step. In another example, a single gas may be introduced, followed by irradiation, and then a second different gas is introduced followed by a second irradiation.

It may be further necessary to recover the aerogel from the system. The aerogel is optionally purged to isolate the aerogel with the use of certain gases e.g. $H_2S$, $SiH_4$, $AsH_3$.

The resulting aerogel has the same structural configuration as the initial aerogel. Thus, the pore structure and pore sizes are maintained. The original pore structure is maintained.

However, some of the functional properties will differ from the initial aerogel. For example, the resulting aerogel may exhibit a change in its initial chemical reactivity characteristics, mechanical properties, abilities to form composite materials, electrical properties, magnetic properties, optical properties, and varying resistance to thermal, chemical and radiation damage. The modified aerogel may demonstrate visible photoluminescence, for example, when excited with ultraviolet light.

Aerogel-based $O_2$ sensors have demonstrated their superiority to detectors based on an organic or inorganic compound suspended in a thin silicone membranes. They exhibit a more rapid response time (due to rapid diffusion of gases through the aerogel pore network), and improved resistance to photobleaching (because the photoluminescence is caused by stable detect centers in $SiO_2$).

An aerogel is produced according to Example 2(a). The aerogel functions as an oxygen sensor. An oxygen sensor based on this technology performs as a lowcost, moderate-sensitivity device operating most effectively in the 0–30% $O_2$ concentration range. The sensor is independent of other gases in the feed gas and of the feed gas flow rate. The prototype sensor successfully operates over a −25° C. to 85° C. temperature range (based on other experimental limitations of the system; the actual usable range is larger). The highest sensitivity is observed at lower temperatures. The prototype uses a Hg-arc lamp for excitation (330 nm) and a Si photodiode for detection of the emission (500 nm). The design is miniatured, and it can be fabricated with built-in pressure and temperature compensation.

The following Examples are provided to further explain and describe the invention. They are not to be construed to be limiting in any way.

General — The materials described herein are available from a number of commercial industrial sources, e.g. Dow Chemical, DuPont, Aldrich Chemical , etc. Specific purities and compositions can be found in *Chemical Sources U.S.A.* published annually by Directories Publications, Inc. of Clemson, S.C. Some particular sources are noted below.

EXAMPLE 1

Preparation Of Aerogels

A two-step, acid-base catalyzed process is used to prepare silica aerogels. Precondensed silica (Silbond H—5, from Silbond Corp.), ethanol (200 proof, from Quantum Corp.), water and 30% $NH_3/H_2O$ is combined at volume ratios of 1:1.67:1.5:0.007, respectively. The resulting wet alcogel is aged for 48 hours in a 40% $H_2O$/ethanol solution with a pH of about 9 ($NH_3$). Water is then removed from the alcogels by repeatedly soaking the alcogel in pure ethanol. The wet alcogel is converted into an aerogel by conventional $CO_2$ substitution and supercritical dying steps (See P.H. Tewari, A.J. Hunt, K.D. Lofftus, *Mater. Lett.* 3, 363 (1985)). The resulting aerogel has a density of about 0.08 g/cm$^3$.

EXAMPLE 2

General Experimental Procedure (a) A silica aerogel is produced according to Example 1, or other such procedures cited supra. The aerogel is placed into a reaction vessel and treated with $H_2$ or $NH_3$ gas. The aerogel is then energized by microwave energy with a frequency of 2.45 GHz and a power of less than 600 W, preferably between about 50 and 100 W. The pressure of the system is maintained at 4 Torr from 5 to 60 minutes. Initially, the system is run at ambient temperature (about 20° C.). The system heats on its own to about 100° C. during the process.

The resulting modified aerogel exhibits a color change from its original colorless appearance to a very pale brown color. The aerogel is otherwise observably identical to the original sample in its size, shape, and transparency. The surface area of the aerogel is 840 m$^2$/g which is essentially identical to the initial aerogel. This observation is further evidence that the internal structure of the aerogel is not physically altered by this process.

By further studying the composition of the aerogel, FIGS. 1A and 1B are NMR spectra where Si MAS-NMR (nuclear magnetic resonance) shows a decrease in $\underline{Si}(OSi=)_4$ ($Q^4$) sites, relative to $\underline{Si}OH(OSi=)_3$ ($Q^3$) sites and $\underline{Si}(OH)_2(OSi=)_2$ ($Q^2$) sites, indicating that the reaction occurs preferentially at strained $Q^4$ sites as opposed to more readily accessible surface ($Q^3$ and $Q^2$) sites. The result of this process is an aerogel composed of sub-stoichiometric silica (SiOx) which contain a large number of oxygen deficient sites.

The mechanical properties of the aerogel are unaffected by this process. However, the optical properties are significantly changed. The material exhibits strong visible photoluminescence when excited with UV (330 nm) light. The wavelength of the emitted light is 460–510 nm (FIG. 2) The intensity of the emitted light is strongly dependent on the concentration of gaseous oxygen within the aerogel.

(b) A titanic (TiO$_2$) aerogel was prepared and treated according to the general process for modification of silica aerogels which is described above in Example 1(a). The mechanical properties remain the same. The modified aerogel exhibits strong visible photoluminescence.

EXAMPLE 3

Alternative Method

A 10 cm³ piece of initial silica aerogel was prepared according to Example 1 or Example 2 above. While maintaining the aerogel environment at ambient temperature and pressure, the aerogel was purged with methane several times. During the purging step, the pressure is adjusted to maintain constant atmosphere of methane at 4 Torr. The sample is irradiated with MW energy for 16 hours at a temperature below or equal to 200° C. The vessel is then filled with air and the sample of aerogel is removed.

The aerogel retains its original shape and does not include cracks. The aerogel is darker in color than the original untreated aerogel. The color of the modified aerogel is dull gray-brown. The sample exhibits visible photoluminescence at 490 nm when excited with ultraviolet (330 nm) light. Chemical analysis further reveals that the sample contains about 1% carbon on a mass basis. This amount corresponds to the amount expected to arise from a thin, monatomic layer of silicon carbide or silicon oxycarbide on the interior surface of the aerogel. Materials such as these are expected to exhibit enhanced chemical and catalytic properties, e.g. high surface area oxides, carbides, nitrides, or combinations thereof.

Control aerogels which are prepared in the same way as the test aerogel above is not treated by the modification process. These control aerogels do not show the presence of carbon.

While only a few embodiments of the invention have been shown and described herein, it will become apparent to those skilled in the art that various modifications and changes can be made in the process to prepare aerogels having novel and specific properties without departing from the spirit and scope of the present invention. All such modifications and changes coming within the scope of the appended claims are intended to be carried out thereby.

I claim:

1. A process to modify the chemical structure of a porous inorganic aerogel under conditions which inhibit plasma formation within the aerogel pores, which process comprises:

(a) providing an initial aerogel with pore sizes of less than 0.1 $\mu$;

(b) exposing said initial aerogel to at least one gas selected from the group consisting of reducing gas, oxidizing gas and combinations thereof, with the proviso that at least one of said reducing gas or said oxidizing gas is present within the pores of the aerogel; and (c) irradiating the combination of step (b) with electromagnetic radiation for between and about 5 and 960 minutes, at a pressure of between about 0.1 and 54 Torr and at an elevated temperature which is sufficient to preserve the structural composition of said initial aerogel wherein a chemically modified aerogel is produced as a result of exposure to said gas and irradiation.

2. The process of claim 1, wherein steps (b) and (c) are repeated one or more times, wherein in step (b) the same gas or a different gas composition is present.

3. The process of claim 1, wherein said irradiation is microwave or radio frequency radiation.

4. The process of claim 3, wherein said irradiation is in contact with a magnetic field which affects the initial aerogel and the modified aerogel.

5. The process of claim 1, wherein said initial aerogel is independently selected from the group consisting of inorganic aerogels consisting of $SiO_2$, $GeO_2$, $SnO_2$, $B_2O_3$, $Al_2O_3$, $TiO_2$, $ZrO_2$, $HfO_2$, $V_2O_5$, $Nb_2O_5$, $Ta_2O_5$, $CrO_3$, $MoO_3$, $WO_3$, $Fe_2O_3$, and lanthanide oxides; carbon; mixed-metal aerogels selected from the group consisting of $SiO_2$—$_{Al_2O_3}$, $SiO_2$—$_{TiO2}$, $BaTiO_3$, $PbTiO_3$, and $NiOAl_2O_3$; and inorganic and mixed-metal aerogel further comprising additional phases.

6. The process of claim 1, wherein said reducing gas is independently selected from the group consisting of $H_2$, $D_2$, $NH_3$, $ND_3$, $N_2$, NO, CO, $CH_4$, $C_2H_6$, $C_2H_2$, $C_3H_8$, $CH_3F$, $B_2H_6$, $B_4H_{10}$, $H_2S$, $H_2Se$, $H_2Te$, $PH_3$, $AsH_3$, $SbH_3$, $SiH_4$, $Si_2H_6$, $SiH_3Cl$, $GeH_4$, $Ge_2H_6$, $SnH_4$, and combinations thereof.

7. The process of claim 1, wherein said oxidizing gas is independently selected from the group consisting of $O_2$, $F_2$, $Cl_2$, $Br_2$, $SF_6$, $NCl_3$, $N_2O$, $PF_3$, $SiHCl_3$, $SiF_4$, $OF_2$, $AsF_5$, and combinations thereof.

8. The process of claim 1 wherein in said process the oxidizing gas or reducing gas or combinations thereof are selected to produce a modified aerogel which has a non oxygen containing inorganic modification to the aerogel structure.

9. The process of claim 1, wherein said initial aerogel exhibits a specific pore structure and said modified aerogel having chemically modified pores exhibits about the same specific pore structure.

10. The process of claim 1, wherein in step (b) said initial aerogel is further exposed to a noble gas to dilete said reducing gas or said oxidizing gas.

11. A process to modify the chemical structure of an aerogel under conditions which inhibit plasma formation within the aerogel pores, which process comprises:

(a) providing an initial aerogel with a pore size of less than 0.1$\mu$ said initial aerogel is selected from the group consisting of inorganic aerogels consisting of $SiO_2$, $GeO_2$, $SnO_2$, $B_2O_3$, $Al_2O_3$, $TiO_2$, $ZrO_2$, $HfO_2$, $V_2O_5$, $Nb_2O_5$, $Ta_2O_5$, $CrO_3$, $MoO_3$, $WO_3$, $Fe_2O_3$ and lanthanide oxides; carbon; mixed-metal aerogels selected from the group consisting of SiO—$Al_2O_3$, $SiO_2$—$TiO_2$, $BaTiO_3$, $PbTiO_3$, and $NiOAl_2O_3$; and inorganic and mixed-metal aerogel further comprising additional phases;

(b) exposing said initial aerogel to at least one gas independently selected from the group consisting of (i) reducing gas selected from the group consisting of $H_2$, $D_2$, $NH_3$, $ND_3$, $N_2$, NO, CO, $CH_4$, $C_2H_6$, $C_2H_2$, $C_3H_8$, $CH_3F$, $B_2H_6$, $B_4H_{10}$, $H_2S$, $H_2Se$, $H_2Te$, $PH_3$, $AsH_3$, $SbH_3$, $SiH_4$, $Si_2H_6$, $SiH_3Cl$, $GeH_4$, $Ge_2H_6$, $SnH_4$, and combinations thereof;

(ii) oxidizing gas independently selected from the group consisting of $O_2$, $F_2$, $Cl_2$, $Br_2$, $SF_6$, $NCl_3$, $N_2O$, $PF_3$, $SiHCl_3$, $SiF_4$, $OF_2$, and $AsF_5$;

(iii) noble gas selected from the group consisting of He, Ne, Ar, Kr, and Xe; and combinations thereof, with the proviso that at least one of said reducing gas or oxidizing gas is present;

(c) irradiating the combination of step (b) with microwave or radio frequency radiation for between about 5 and 960 minutes at a pressure of between about 0.1 and 54 Torr and at an elevated temperature which is sufficient to preserve the structural composition of said aerogel; and (d) producing an aerogel which is chemically modified.

12. The process of claim 10, wherein said initial aerogel exhibits a specific pore structure and said modified aerogel exhibits essentially the same specific pore structure.

13. The process of claim 11, wherein steps (b) and (c) are repeated one or more times, wherein in step (b) the same gas or a different gas composition is present.

14. The process of claim 10 wherein in step (a) the aerogel is selected from the group consisting of $SiO_2$, $Al_2O_3$, $TiO_2$, $ZrO_2$, and combinations thereof;

in step (b) the reducing gas is selected from the group consisting of $H_2$, $NH_3$, and CO;

in step (b) the oxidizing gas is selected from the group consisting of $F_2$, $Cl_2$, and combinations thereof; and in step (b) the noble gas is selected from the group consisting of Ne, Ar, and combinations thereof.

15. The process of claim 14 wherein in step (c) the radio frequency radiation is used.

16. The process of claim 11 wherein in step (a) the aerogel is a silica aerogel;

in step (b) the reducing gas is selected from the group consisting of hydrogen, carbon monoxide, and ammonia, and in step (c) the radiation is microwave radiation.

17. The process of claim 10 wherein in step (a) the aerogel is a silica aerogel;

in step (b) the oxidizing gas is selected from the group consisting of oxygen and fluorine; and in step (c), the radiation is microwave radiation.

* * * * *